United States Patent
Liu et al.

(10) Patent No.: US 12,351,958 B2
(45) Date of Patent: Jul. 8, 2025

(54) APPARATUS AND PROCESS FOR DEFORMING A WEB

(71) Applicant: The Procter & Gamble Company, Cincinnati, OH (US)

(72) Inventors: Xiaoxin Liu, Beijing (CN); Tong Tong, Beijing (CN); Kun Sun, Beijing (CN); Xiaohui Dong, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/502,188

(22) Filed: Oct. 15, 2021

(65) Prior Publication Data
US 2022/0136153 A1    May 5, 2022

(30) Foreign Application Priority Data

Oct. 30, 2020  (WO) ................ PCT/CN2020/125264
Jul. 23, 2021  (WO) ................ PCT/CN2021/108207

(51) Int. Cl.
| | | |
|---|---|---|
| *D04H 1/541* | (2012.01) | |
| *A61F 13/15* | (2006.01) | |
| *D04H 1/407* | (2012.01) | |

(52) U.S. Cl.
CPC ....... *D04H 1/541* (2013.01); *A61F 13/15577* (2013.01); *D04H 1/407* (2013.01);
(Continued)

(58) Field of Classification Search
None
See application file for complete search history.

(56) References Cited

U.S. PATENT DOCUMENTS

| 6,673,418 B1 | 1/2004 | DeOlivera et al. |
| 7,553,532 B2 | 6/2009 | Turner et al. |

(Continued)

FOREIGN PATENT DOCUMENTS

| CN | 206324925 U | 7/2017 |
| JP | S4932887 A | 3/1974 |

(Continued)

OTHER PUBLICATIONS

PCT Search Report and Written Opinion for PCT/CN2021/108207 dated Oct. 28, 2021.
All Office Actions; U.S. Appl. No. 17/510,660, filed Oct. 26, 2021.
Unpublished U.S. Appl. No. 17/510,660, filed Oct. 26, 2020, to Xiaoxin Liu et al.

*Primary Examiner* — Shawn Mckinnon
(74) *Attorney, Agent, or Firm* — Anna E. Haller; Amanda Marie Herman Berghauer

(57) ABSTRACT

The present invention relates to an apparatus for deforming a web to created deformed nonwoven which comprises a pair of counter-rotating rolls that form a nip therebetween, the pair of rolls comprising: a first roll comprising a surface, a plurality of protrusions extending radially outwardly from the surface of the first roll, and a plurality of concaves formed inwardly from the surface of the first roll; and a second roll comprising a surface; and a process for producing a deformed web comprising the steps of (a) forming a fibrous web; (b) subjecting the fibrous web to bonding treatment to bond at least part of fibers constituting the fibrous web to obtain a precursor nonwoven; and (c) subjecting the precursor nonwoven to a deformation forming unit comprising an apparatus according to the present invention.

18 Claims, 9 Drawing Sheets

(52) U.S. Cl.
CPC ............... *A61F 2013/15934* (2013.01); *D10B 2509/026* (2013.01)

(56) References Cited

U.S. PATENT DOCUMENTS

| | | | |
|---|---|---|---|
| 10,045,888 B2 | 8/2018 | Strube et al. | |
| 2008/0108962 A1* | 5/2008 | Furuta | B32B 7/05 604/367 |
| 2012/0276238 A1* | 11/2012 | Strube | A61F 13/15731 425/336 |
| 2016/0067118 A1 | 3/2016 | Hammons et al. | |
| 2016/0278986 A1 | 9/2016 | Gross et al. | |
| 2018/0221220 A1 | 8/2018 | Kuramochi | |
| 2019/0053958 A1 | 2/2019 | Kurihara et al. | |
| 2019/0060140 A1 | 2/2019 | Oshima et al. | |
| 2020/0375820 A1 | 12/2020 | Tagomori | |
| 2023/0124706 A1 | 4/2023 | Kasparkova | |

FOREIGN PATENT DOCUMENTS

| | | |
|---|---|---|
| JP | 2004194815 A | 7/2004 |
| JP | 2007175093 A | 7/2007 |
| JP | 2011137246 A | 7/2011 |
| JP | 2012090689 A | 5/2012 |
| WO | 2004080341 A2 | 9/2004 |
| WO | 2007144469 A1 | 12/2007 |
| WO | 2009105000 A1 | 8/2009 |
| WO | 2012148935 A1 | 11/2012 |
| WO | 2013005782 A1 | 1/2013 |
| WO | 2016040120 A1 | 3/2016 |
| WO | WO2016040120 * | 3/2016 |
| WO | 2017149792 A1 | 9/2017 |
| WO | 2017156162 A1 | 9/2017 |
| WO | 2017209009 A1 | 12/2017 |
| WO | 2018004478 A1 | 1/2018 |

* cited by examiner

APPARATUS AND PROCESS FOR DEFORMING A WEB

FIELD OF THE INVENTION

The present invention relates to apparatuses and processes for deforming a web to create such materials.

BACKGROUND OF THE INVENTION

Nonwovens including synthetic fibers formed from thermoplastic resin are widely used as sheets constituting absorbent articles such as sanitary napkins, infant disposable diapers, personal care disposable diapers, and the like.

These absorbent articles comprise several layers providing different functions. A liquid permeable topsheet is disposed closest to the wearer's skin and should be capable of quickly absorbing the excreted fluid. A backsheet is disposed on the opposed, garment-facing side of the article. Some absorbent articles in the market further comprises a nonwoven outermost layer forming at least part of a garment-facing surface of an absorbent article. Other components of absorbent articles are well known, and include in particular an absorbent core disposed between the topsheet and the backsheet to absorb and retain the excreted fluids.

Three-dimensional nonwovens comprising three-dimensional elements can provide craftsmanship perception. Three-dimensional substrates may also provide improved fluid handling properties, and improved sensory feels such as skin softness, and cushion feel, etc.

In some configurations, nonwovens are supplied on rolls and moved to an absorbent article manufacturing location. During the absorbent article assembly process, nonwovens are unwound from the rolls and supplied to an assembly line that converts the nonwoven of material into absorbent articles. In some instances, nonwovens may be relatively tightly wound on the rolls, and as such, the associated high winding pressures may compress nonwoven webs, resulting in a reduced caliper. Such compressed nonwoven webs when incorporated into an absorbent article may have a thin appearance that conveys a message of reduced softness to a consumer and/or may be aesthetically unpleasing. They may also negatively affect various performances such as fluid handling properties of the nonwoven webs. To mitigate the problems associated with nonwoven compression, some manufacturers may apply heat to the nonwoven once unwound from the rolls. In turn, the application of heat to some types of nonwoven may increase the caliper or volume of the nonwovens, referred to herein as "relofting".

There is a continuous need for method and apparatus that are capable of forming cost effective nonwoven which can create and maintain well perceivable three dimensional appearance.

SUMMARY OF THE INVENTION

The present invention provides an apparatus for deforming a web to created deformed nonwoven which comprises a pair of counter-rotating rolls that form a nip therebetween, the pair of rolls comprising: a first roll comprising a surface, a plurality of protrusions extending radially outwardly from the surface of the first roll, and a plurality of concaves formed inwardly from the surface of the first roll; and a second roll comprising a surface.

The present invention also provides a process for producing a deformed nonwoven comprising the steps of (a) forming a fibrous web; (b) subjecting the fibrous web to bonding treatment to bond at least part of fibers constituting the fibrous web to obtain a precursor nonwoven; and (c) subjecting the precursor nonwoven to a deformation forming unit comprising a pair of a pair of rolls that form a nip therebetween to form a three dimensional nonwoven, the pair of rolls comprising: a first roll comprising a surface, a plurality of protrusions extending radially outwardly from the surface of the first roll, and a plurality of concaves formed inwardly from the surface of the first roll; and a second roll comprising a surface.

These and other features, aspects, and advantages of the present invention will become.

DETAILED DESCRIPTION OF THE INVENTION

Figure 1:
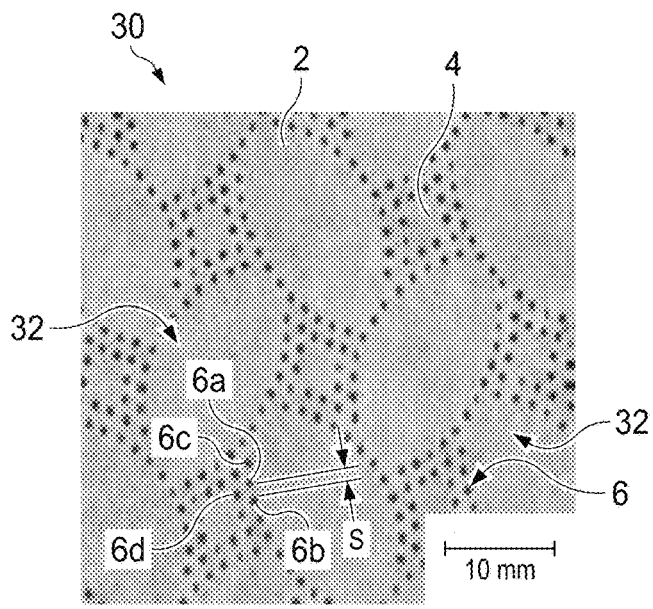
FIG. 1 is a plan view of a nonwoven.

All ranges are inclusive and combinable. The number of significant digits conveys neither limitations on the indicated amounts nor on the accuracy of the measurements. All numerical amounts are understood to be modified by the word "about" unless otherwise specifically indicated.

The term "absorbent articles", as used herein, include disposable diapers, sanitary napkins, panty liners, incontinence pads, interlabial pads, breast-milk pads, sweat sheets, animal-use excreta handling articles, animal-use diapers, and the like.

The term "aperture", as used herein, refers to a hole. The apertures can either be punched cleanly through the web so that the material surrounding the aperture lies in the same plane as the web prior to the formation of the aperture (a "two dimensional" aperture), or holes formed in which at least some of the material surrounding the opening is pushed out of the plane of the web. In the latter case, the apertures may resemble a protrusion or depression with an aperture therein, and may be referred to herein as a "three dimensional" aperture, a subset of apertures.

The term "component" of an absorbent article, as used herein, refers to an individual constituent of an absorbent article, such as a topsheet, secondary layer, acquisition layer, liquid handling layer, absorbent core or layers of absorbent cores, and backsheets.

The term "cross-machine direction" or "CD" means the path that is perpendicular to the machine direction in the plane of the web.

The term "deformable material", as used herein, is a material which is capable of changing its shape or density in response to applied stresses or strains.

The term "discrete", as used herein, means distinct or unconnected. When the term "discrete" is used relative to forming elements on a roll, it is meant that the distal (or radially outwardmost) ends of the forming elements are distinct or unconnected in all directions, including in the machine and cross-machine directions (even though bases of the forming elements may be formed into the same surface of a roll, for example).

The term "forming elements", as used herein, refers to any elements on the surface of a roll that are capable of deforming a web. The term "forming elements" includes both continuous or non-discrete forming elements such as the ridges and grooves on ring rolls, and discrete forming elements.

The term "machine direction" or "MD" means the path that material, such as a web, follows through a manufacturing process.

Three-Dimensional Nonwoven

The apparatus according to the present invention is suitable for deforming a web to obtain three-dimensional nonwovens.

The web that will be deformed can comprise any suitable deformable material, such as a woven, nonwoven, film, combination, or laminate of any of the foregoing materials.

As used herein, the term "nonwoven" or "nonwoven" refers to a web having a structure of individual fibers or threads which are interlaid, but not in a repeating pattern as in a woven or knitted fabric, which do not typically have randomly oriented fibers. Nonwoven or fabrics have been formed from many processes, such as, for example, melt-blowing, spunbonding, hydroentangling, airlaid, wetlaid, through-air-dried paper making processes, and bonded carded web processes, including carded thermal bonding. The nonwoven can comprise unbonded fibers, entangled fibers, tow fibers, or the like. Fibers can be extensible and/or elastic, and may be pre-stretched for processing. Fibers can be continuous, such as those produced by spunbonded methods, or cut to length, such as those typically utilized in a carded process. Fibers can be bicomponent, multiconstituent, shaped, crimped, or in any other formulation or configuration known in the art for nonwoven and fibers. In general, the fibers can be bondable, either by chemical bond (e.g. by latex or adhesive bonding), pressure bonding, or thermal bonding. If thermal bonding techniques are used in the bonding process described below, a certain percentage of thermoplastic material, such as thermoplastic powder or fibers can be used.

Figure 2:
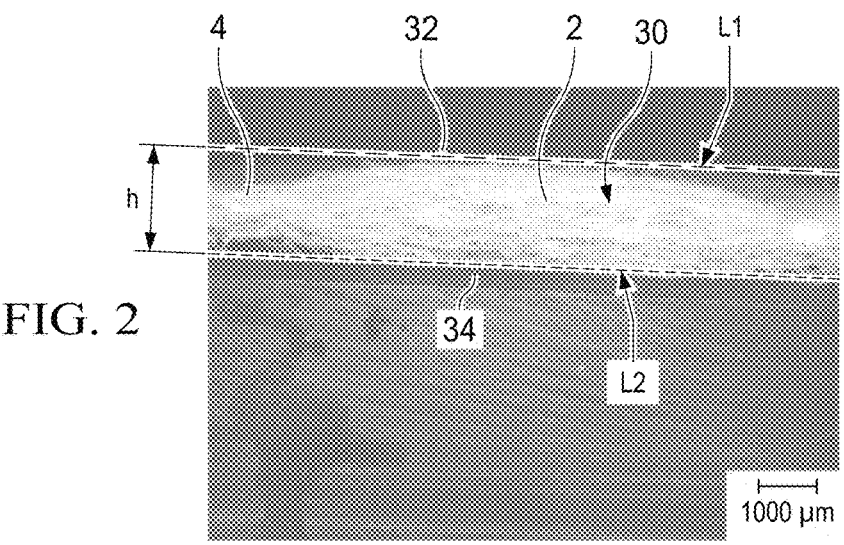
FIG. 2 is a cross-section view of the nonwoven of FIG. 1.
Figure 3:
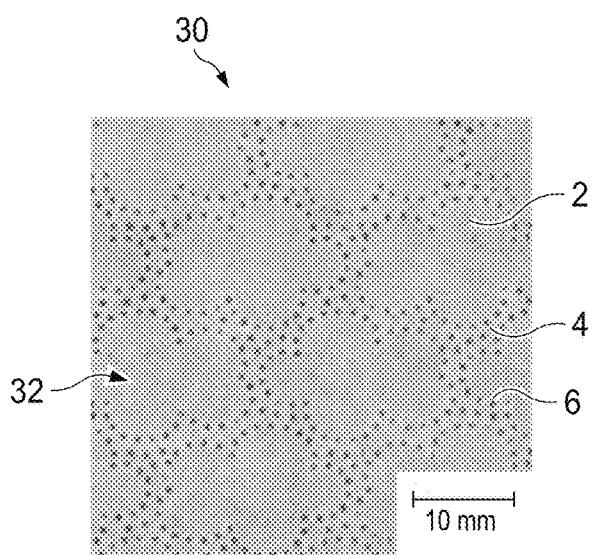
FIG. 3 is a plan view of another exemplary nonwoven.
Figure 4:
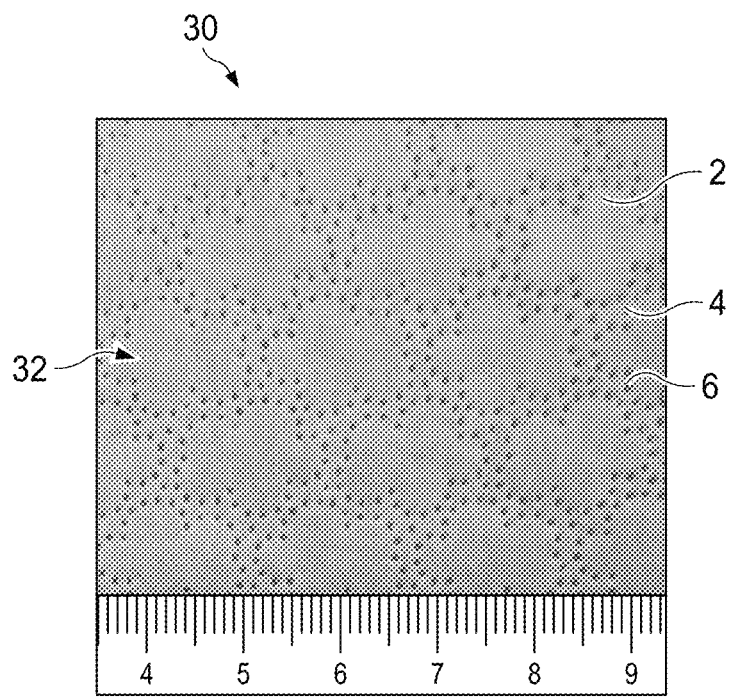
FIG. 4 is a plan view of another exemplary nonwoven.

Three-dimensional nonwovens are suitable for a component of an absorbent article. FIG. 1 shows a plan view of a three-dimensional nonwoven which can be provided by an apparatus and/or a process of the present invention. FIG. 2 shows a cross section view of the nonwoven in FIG. 1. FIGS. 3 and 4 are plan views of another exemplary three-dimensional nonwovens provided by an apparatus and/or a process of the present invention.

Referring to FIGS. 1 and 2, the three-dimensional nonwoven 30 produced by the apparatus of the present invention comprises a first side 32, a second side 34 opposite the first side 32, at least one protrusion 2. The protrusion 2 provides a three-dimensional profile to the nonwoven 30. The protrusion 2 be in any shape, for example, a circles, an ellipse, a triangle, a polygon, a flower, a heart, a cloud, and the like.

The protrusion is filled with fibers, and has substantially no hollow space underneath. As the protrusion is filled with fibers, the nonwoven may maintain three-dimensional structure stably under compression, and enhance fluid transfer to an adjacent layer when the nonwoven is used as a component of an absorbent article.

The protrusion may coordinate with graphics, indicia, printing, inks, color, and/or patterned adhesives, for example, located in the nonwoven or in another component of an absorbent article when it is used as a component of an absorbent article.

Referring to FIGS. 1 and 2, three-dimensional nonwoven 30 produced by the apparatus of the present invention further comprises a recess 4. The recess 4 may comprise a plurality of deformations which may comprises apertures, embossings or a combination thereof. In one embodiment, the recess 4 comprises a plurality of apertures as shown in FIGS. 1 and 2.

Deformations may be in any of circular, oval, hour-glass shaped, star shaped, polygonal and the like, and combinations thereof. Polygonal shapes include, but are not limited to triangular, quadrilateral, hexagonal, octagonal or trapezoidal. In one embodiment, deformations are circular. In another embodiment, deformations are an oval shape. deformations may have a size in a range of about 0.1 mm$^2$-about 3 mm$^2$, or in a range of about 0.2 mm$^2$-about 2 mm$^2$, or in a range of about 0.3 mm$^2$-about 1.5 mm$^2$. The recess may have deformations having the same size and/or shape. The recess may have deformations having different sizes and/or shapes.

The recess 4 may comprise deformations forming a pattern. A pattern formed by deformations may be any shape of pattern, for example, a shape of one or multiple linear lines or curved lines, a circles, an ellipse, a triangle, a polygon, a flower, a cloud, and the like. The pattern may be a regular, homogeneous and uniform pattern or an irregular, non-uniform and non-homogeneous pattern. In some embodiments, nonwoven disclosed herein comprises a plurality of recesses, wherein deformation patterns in the recesses are not necessarily in the same shape or size. That is, a deformation pattern in one recess may differ from a deformation pattern in another recess in the nonwoven disclosed herein. Patterns may be various shapes and/or various sizes. The nonwoven disclosed herein may have uniform deformation patterns.

In some embodiments, a recess comprises clustered deformations. The term "clustered deformations" herein intends to mean a deformation pattern wherein at least one deformation having at least three adjacent deformations wherein the one deformation and each of the at least three adjacent deformations has an edge-to-edge space S (shortest space between an edge of one deformation to an edge of an adjacent deformation) no greater than about 3 mm Referring to FIG. 1, the recess 4 comprises aperture 6a having at least 3 adjacent apertures 6b, 6c and 6d where each edge-to-edge space S between aperture 6a and each of apertures 6b, 6c is about 0.60 mm.

FIG. 3 is another examples having at least one recess having clustered deformations.

Without wishing to be bound by theory, it is believed that clustered deformations in the recess work like anchor points in the nonwoven and restrain nonwoven from regain its bulkiness which helps form a clear three-dimensional structure as having a distinctive caliper difference between the protrusion and the recess. In addition, clustered deformations in the recess work like anchor points in the nonwoven and require more work input to compress the nonwoven in comparison with non-deformed nonwoven.

The deformation pattern in a recess may coordinate with graphics, indicia, printing, inks, color, and/or patterned adhesives, for example, located in the nonwoven or in another component of the absorbent article when it is used as a component of an absorbent article.

When the three-dimensional nonwoven 30 comprises a plurality of protrusions 2, each of the protrusions may be substantially surrounded by the recess. Substantially surrounded herein intents to mean that at least 80% of periphery of the protrusion is surrounded by the recess. In another embodiment, the three-dimensional nonwoven 30 comprises a plurality of recesses 4.

Figure 5A:
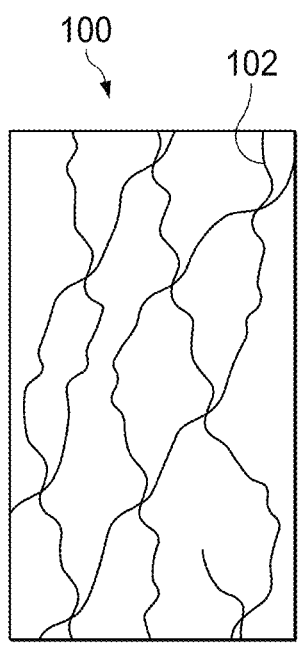
FIG. 5A-5C are schematic illustrations of a shape-memory effect.
Figure 5B:
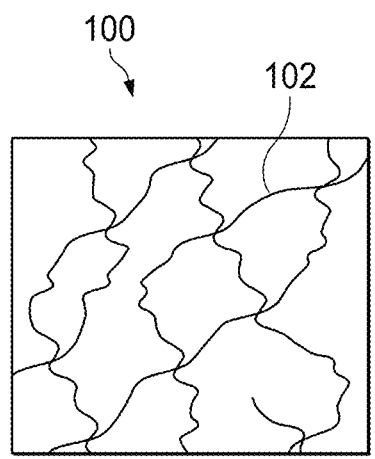
Figure 5C:
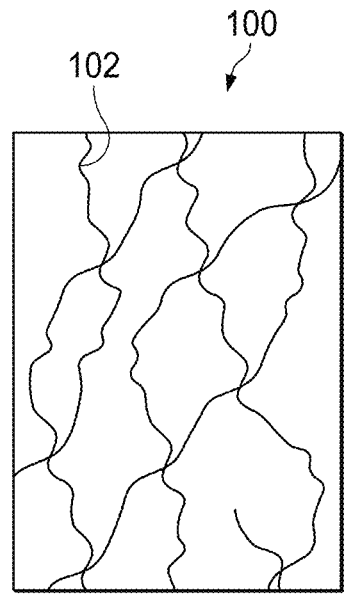

The nonwoven may comprise shape memory fibers having shape memory effect. A shape memory effect is the capability of a material to recover its shape upon application of an external stimulus. A shape memory effect and shape memory fibers have been reported in publications such as Shape-Memory Polymers, Angew. Chem. Int. Ed. 2002, 41, 2034-2057, and Recent advances in shape memory polymers and composites: a review, J Mater Sci (2008) 43:254-269. The shape recovery caused by a change in temperature is called a thermally induced shape-memory effect. Referring to FIGS. 5A-5C, a material 100 comprising fibers 102 comprising shape memory polymer, when conventionally processed such as thermally and/or mechanically processed, receives its permanent shape (FIG. 5A). Afterwards, when the material 100 is deformed, for example the material 100 is compressed, and the intended temporary shape is fixed (FIG. 5B). The permanent shape is now stored in the material 100 while the material 100 shows the temporary shape. Heating up the material 100 above a transition temperature of shape memory fibers 102 constituting the material 100 induces the shape memory effect and results in the recovery of the stored, permanent shape (FIG. 5C).

The nonwoven may comprises a thermoplastic conjugate fiber comprising a first polymer component and a second polymer component having a lower melting point than the melting point of the first polymer component, wherein the first polymer component is present on at least part of the surface of the conjugate fiber in a lengthwise continuous configuration. The nonwoven may comprise a fiber comprising a polymer selected from the group consisting of polyethylene terephthalate, polytrimethylene terephthalate, polybutylene, polyethylene terephthalate copolymer, poly (tetramethylene ether) glycol, and combinations. One type or a plurality of types can be selected, based on the application of the nonwoven.

Thermoplastic conjugate fibers suitable for the nonwoven may have two-dimensional crimps and/or three-dimensional crimps. Herein, the term "two-dimensional crimp" can be understood mechanical crimping in which the peaks of the crimped fiber are sharply angled. Three-dimensional crimp may refer to crimp where the peaks are curved (wave shaped crimping) or spiral (spiral shaped crimping), crimp where both wave shaped crimping and spiral shaped crimping exist, or crimp where both mechanical crimp and at least one of wave and spiral shape crimps exist. In one embodiment, the core/sheath composite fiber has two-dimensional crimps which is cost-effective compared to a composite fiber having three-dimensional crimps.

Thermoplastic fibers suitable for the present invention may be a thermoplastic homopolymer fiber.

A basis weight of the three dimensional nonwoven may be appropriately selected depending on the nonwoven application. For the nonwoven disclosed herein as a topsheet of an absorbent article, the nonwoven may be from about 25 $g/m^2$ to about 100 $g/m^2$, or from about 35 $g/m^2$ to about 70 $g/m^2$. For the use of the nonwoven as a topsheet of an absorbent article, in one embodiment, the integral basis weight of the nonwoven is in the range of from about 30 $g/m^2$ to about 70 $g/m^2$, or from about 35 $g/m^2$ to about 55 $g/m^2$.

Apparatus

Figure 7:
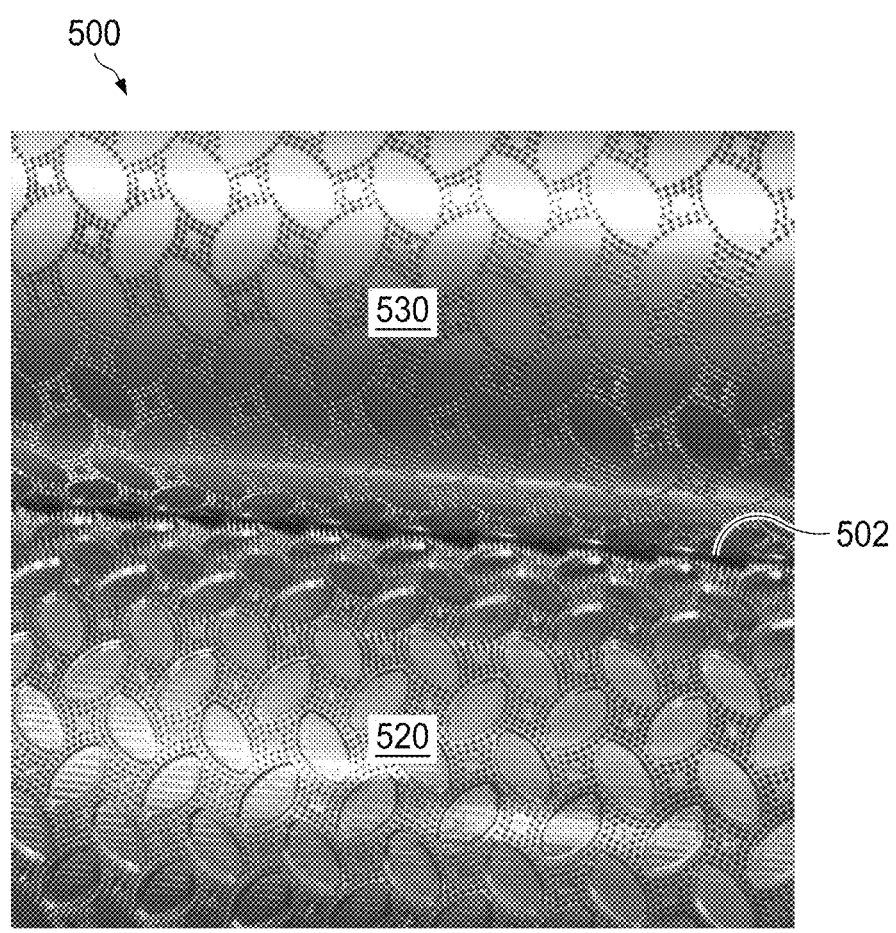
FIG. 7 is a view of intermeshing engagement of portions of a pair of rolls in accordance with the present disclosure.

Referring to FIG. 7 an apparatus according to the present invention comprises a pair of counter-rotating rolls 500 having two intermeshing rolls, a first roll 520 and a second roll 530 that form a nip 502 therebetween.

Figure 8:
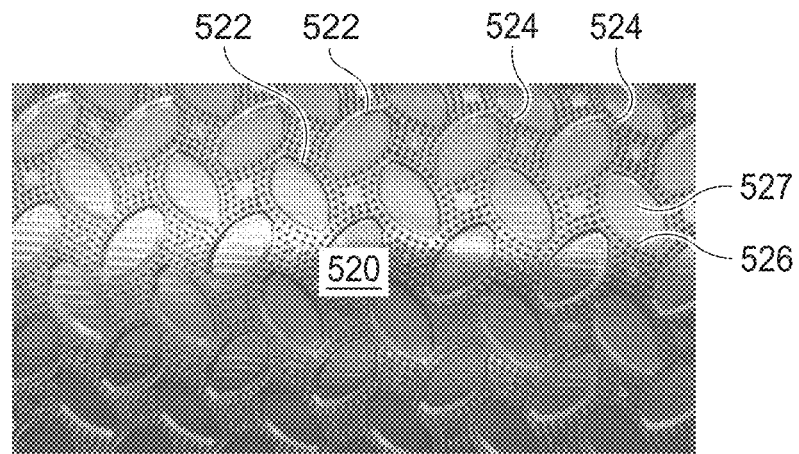
FIG. 8 is a view of a portion of the first roll in the pair of rollers in FIG. 7.
Figure 9:
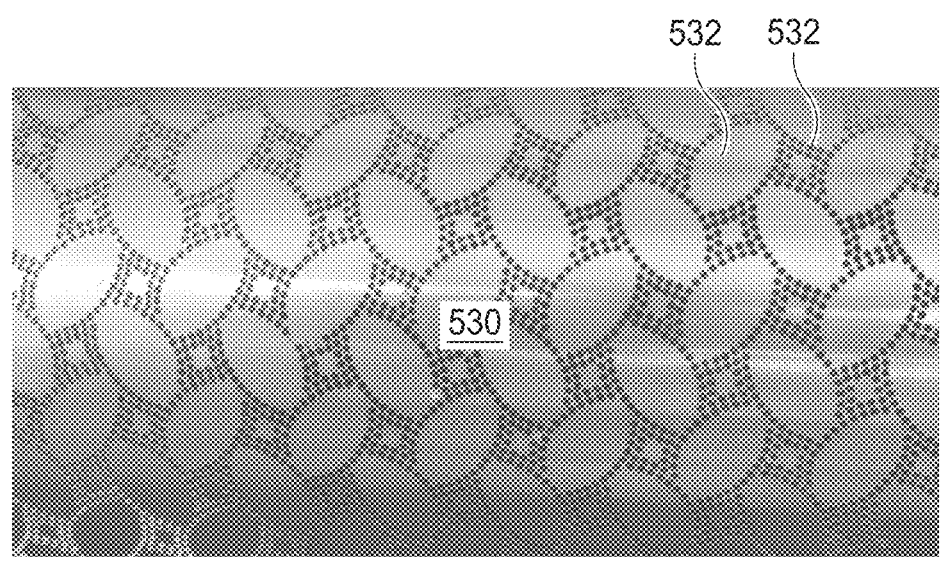
FIG. 9 is a view of a portion of the second roll in the pair of rollers in FIG. 7.

FIG. 7 shows a view of intermeshing engagement of portions of an exemplary first and a second rolls in the pair of rolls. FIG. 8 and FIG. 9 are views of portions of the first roll 520 and a portion of the second roll 530, respectively.

Referring to FIG. 8, the first roll 520 comprises a surface 522, a plurality of projections 524 extending radially outwardly from the surface 522 of the first roll 520, and a plurality of first concaves 526 formed inwardly from the surface 522 of the first roll 520, each of the first concaves 526 having a recess bottom 527. The first concave 526 may be discrete in an MD and a CD, and discontinuous as shown in FIG. 8. In one embodiment, still referring to FIG. 8, at least one of the first concaves 526 is substantially surrounded by some of the plurality of the projections 524.

The second roll 530 comprises a smooth surface. The second roll 530 may be an anvil roll with a smooth surface. Referring to FIG. 9, the second roll 530 comprises a surface 532 and may further comprise a plurality of recesses 534 formed inwardly from the surface 532 of the second roll 530 which defining at least one zone 536. When the second roll 530 comprises a plurality of zones 536, referring to FIG. 9, the zones 536 may be discrete in an MD and a CD, and discontinuous.

The projection 524 in the first roll may be a forming element which can form emboss or an aperture on a web in combination with the second roll as shown in FIGS. 7 and 8. The concave 526 in the first roll 520 is configured to at least partially the surface 532 (or zone 536) of the second roll 530, thereby creating a protrusion 2 in nonwoven 30. The concave 526 has a depth so that a portion of the nonwoven forming a protrusion will be less compressed than other portions of the nonwoven. Specifically, as the concave 526 in the first roll 520 engages with the surface 532 (or zone 536) of the second roll 530, there is a sufficient space between the first side of the nonwoven and the surface of the concave 526 in a rotational axial direction. This feature enables the protrusion 2 in nonwoven 30 to have a distinctive height as well as a soft and cushiony feel in comparison with a case when portions in the first roll 520 corresponding to the concaves 526 are flat, i.e., in the same level as the surface of the first roll 520 instead of being concaved. The concaves may have a depth no less than about 0.5 mm, or no less than about 0.7 mm, or no less than about 1.0 mm as measured according to Concave Depth Test.

The concaves may have an area no less than about 50 $mm^2$, or no less than about 70 $mm^2$, or no less than about 100 $mm^2$ as measured according to Concave Area Test. If the area of concave 526 is too small, it may increase direct heating of a first side 32 of the nonwoven facing the surface of the first roll 520 which causes overheat of the nonwoven, so that the first side 32 of the nonwoven becomes flat and may not create desirably recognizable three-dimensional perception in the first side 32 of the nonwoven.

Having the concave 526, the first roll 520 and the second roll 530 can create a height difference between the protrusion 2 and the compressed recess 4 in a nonwoven 30 when a precursor nonwoven passes through the nip 502 which determines a permanent shape of the nonwoven. As the protrusion 2 can have a permanent shape with a greater height than the case when portions in the first roll 520 corresponding to the concaves 526 are flat, the protrusion 2 can recover a three-dimensional shape in a high rate under heat condition even it is compressed in package, storage, or in converting.

In one embodiment, nonwoven 30 has a shape memory index no less than about 110%, or no less than about 115%, or no less than about 120%, so that the protrusion 2 can more effectively recover a three-dimensional shape in a high rate under heat condition even it is compressed.

In one embodiment, referring to and FIGS. 1-2 and FIGS. 8-9, a first roll 520 may create the protrusion 2 and the recess 4 having a plurality of apertures 6 in the nonwoven 30 in combination with the second roll.

The recesses 534 in the second roll 530 may be configured to at least partially receive the projections 524 in the first roll 520 thereby creating the apertures 6 in the precursor nonwoven 20 when the precursor nonwoven 20 passes through a nip 502 formed by the first roll 520 and the second roll 530.

Figure 10:
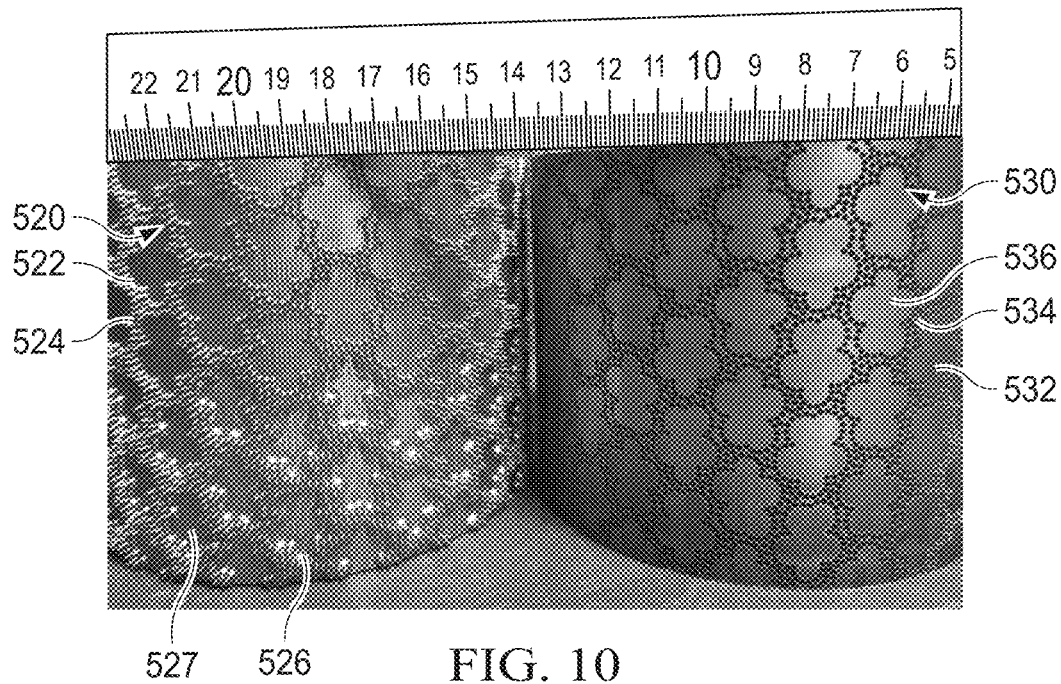
FIG. 10 show another first roll and a second roll.
Figure 11:
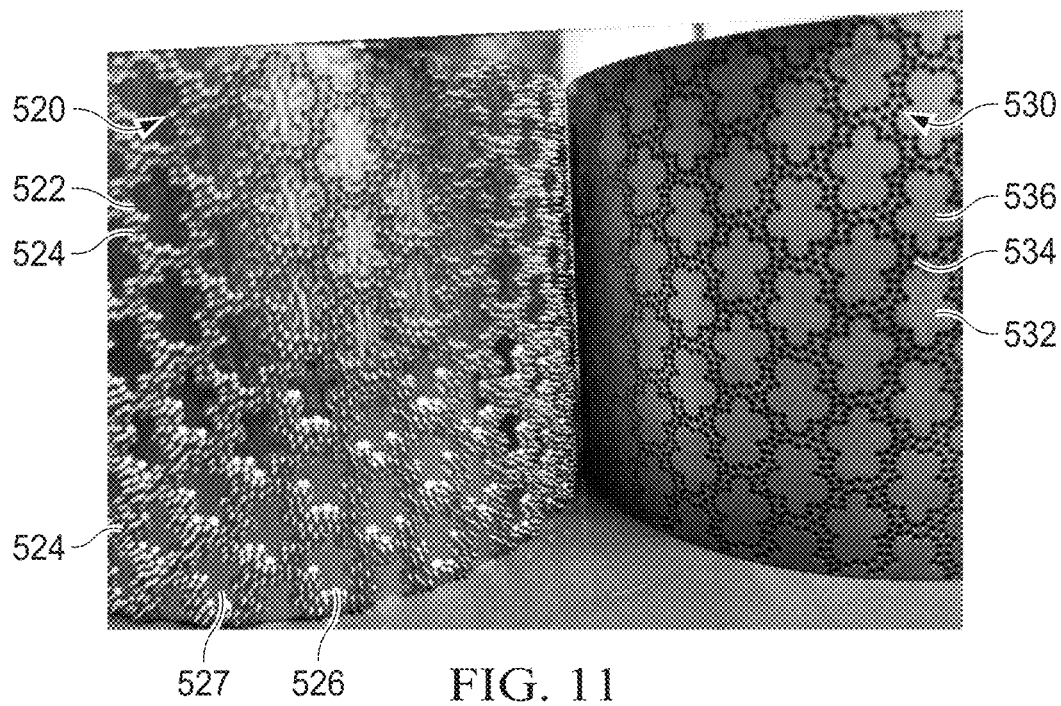
FIG. 11 show another first roll and a second roll.

Each of FIGS. 10 and 11 shows a first roll 520 and a second roll 530 which can constitute a pair of roll together and form a nip 502 therebetween. The first roll 520 has features according to the present invention in the bottom half while conventional features in the upper half. That is, the bottom half of the first roll 520 comprises a surface 522, a plurality of projections 524, and a plurality of concaves 526 which have a concave bottom 577, and the upper half of the first roll 520 has a surface 522 and a plurality of projections 524. In the upper half of the first roll 520, the flat areas surrounded by the projections 524 are in the same level as the surface of the first roll 520.

Referring to FIGS. 7-9, and FIGS. 10 and 11, intermeshing engagement of the first roll 520 and the second roll 530, when a precursor nonwoven 20 passes through a nip 502 formed by the first roll 520 and the second roll 530, create at least one protrusion 2, and at least one recess 4 comprising a plurality of apertures 6.

Nonwoven Manufacturing Process

A process for producing a three-dimensional nonwoven according to the present invention comprising the steps of (a) forming a fibrous web; (b) subjecting the fibrous web to bonding treatment to bond at least part of fibers constituting the fibrous web to obtain a precursor nonwoven; and (c) subjecting the precursor nonwoven to a deformation forming unit comprising an apparatus according to the present invention. The deformation forming unit comprises a pair of a pair of rolls that form a nip therebetween to form a three dimensional nonwoven, the pair of rolls comprising: a first roll comprising a surface, a plurality of projections extending radially outwardly from the surface of the first roll, and a plurality of concaves formed inwardly from the surface of the first roll; and a second roll comprising a surface.

The fibrous web may be carded webs such as parallel webs, semi-random webs, random webs, cross-webs, criss-cross webs, and the like, air-laid webs, wet-laid webs, and spunbond webs, and the like.

In some embodiments, the fibrous web may be a composite web having at least two web layers. A composite fibrous web can be formed using parallel carding machines by laying a first fibrous web on a conveyor belt and overlaying a second fibrous web on the first fibrous web. In other embodiments, a composite fibrous web is formed using parallel carding machines by laying a second fibrous web on a conveyor belt and overlaying a first fibrous web on the second fibrous web. The first fibrous web may form a first side of the three-dimensional nonwoven, and the second fibrous web may form a second side of the three-dimensional nonwoven. The first fibrous web laid down facing the conveyor belt may ensure that the three-dimensional nonwoven to have a smooth first side with little fuzz concern when the three-dimensional nonwoven is used as a topsheet in an absorbent article in such a way that the first side of the three-dimensional nonwoven forms at least part of a skin-facing surface of the absorbent article.

The bonding treatment of a fibrous web can be conducted using any conventionally known fiber bonding method. Examples of such a bonding method include hot air through-type thermal bonding and ultrasonic bonding.

Figure 6:
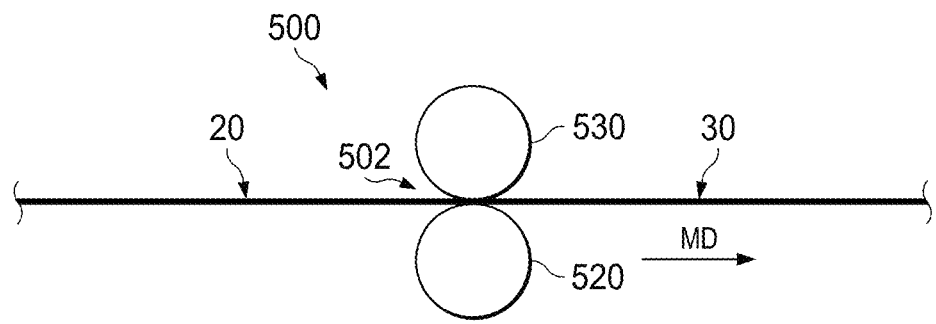
FIG. 6 is a schematic illustration of an exemplary process for producing deformed nonwovens of the present disclosure.

Referring to FIG. 6, precursor nonwoven 20 may be deformed by passing it through a nip 502 formed by a pair of rolls 500 having two intermeshing rolls 520 and 530, to form a three-dimensional nonwoven 30. At least one of the rolls 520 and 530 may be heated. FIG. 7 shows a view of intermeshing engagement of portions of an exemplary first and a second rolls in the pair of rolls.

As the concave 526 in the first roll 520 engages with the surface 532 (or zone 536) of the second roll 530, there is a sufficient space between the first side 32 of the nonwoven 30 and the surface of the concave 526 in a rotational axial direction so that the nonwoven 30 has greater height as well as a soft and cushiony feel compared to a case when portions in the first roll 520 corresponding to the concaves 526 are flat.

Having the concave 526, the first roll 520 and the second roll 530 can create a height difference between the protrusion 2 and the recess 4 when the precursor nonwoven 20 passes through the nip 502 which determines a permanent shape of the nonwoven 30. As the protrusion 2 has a permanent shape with a greater height than the case when portions in the first roll 520 corresponding to the concaves 526 are flat, the protrusion 2 can recover a three-dimensional shape in a high rate under heat condition even it is compressed in package, storage, or in converting.

The process of the present invention may further comprise a relofting step to increase bulkiness of the nonwoven and enhance three-dimensional appearance of the nonwoven.

Relofting process is a process to make a nonwoven regain its bulkiness by providing energy to the nonwoven. Relofting process may be conducted via various processes known to those skilled in the art. A heating source includes oven, burner, or infrared radiation, producing heat to increase the temperature of the nonwoven. As the temperature increases, fibers within the nonwoven begin to soften, and at least some of the fibers begin to realign with, and/or detach from, the fibers. The realigning and/or detaching fibers cause the nonwoven to increase in caliper, thereby decreasing the density of the nonwoven. The final relofted caliper is dependent upon the temperature and the residence time, which is the overall time that the nonwoven is exposed to the increased temperature in the relofting process.

The reloft step may be proceeded by subjecting the deformed nonwoven to a heating unit to increase bulkiness of the deformed nonwoven.

In one embodiment, relofting a nonwoven can be conducted in accordance with methods disclosed in PCT/US2019/066455 filed on Sep. 5, 2019. The PCT application is hereby incorporated herein by reference in its entirety unless expressly excluded or otherwise limited.

In another embodiment, relofting a nonwoven can be conducted by heating the nonwoven in an oven applying hot air.

Test Methods

1. Nonwoven Height Test (1) Sample Preparation

If a nonwoven is available in its raw material form, a specimen with the size about 25 mm×25 mm or a bigger size is cut from the raw material to include at least one complete a protrusion and part of two adjacent recesses. If a nonwoven is a component layer such as a topsheet of an absorbent article, the absorbent article this size is cut and the nonwoven layer is removed from the absorbent article, using a razor blade to excise the nonwoven layer from the underling layers of the absorbent article. A cryogenic spray (such as Cyto-Freeze, Control Company, Houston TX) or other suitable solvents that do not permanently alter the properties of the nonwoven layer composition may be used to remove the nonwoven layer specimen from the underling layers if necessary. Any remaining adhesive may be removed from the specimen by the following steps using Tetrahydrofuran (THF) as solvent.

1) In a hood, transfer 1 liter of THF into the 3-4 liter beaker.
2) Submerge specimen in the 1 liter of THF.
3) Place beaker on shaking table and stir gently for 15 minutes and keep solution with sample sit for 5 additional minutes.
4) Take specimen out of THF solution, and carefully squeeze THF solution out of specimen.
5) Let specimen air dry in hood for a minimum of 15 minutes.

To obtain a nonwoven cross section specimen, the nonwoven is laid on a flat bench with a first side upward, and is cut along line 2-2 so as to cut the protrusion 2 in its apex height and sandwiched the cut protrusion 2 between recesses 4, referring to FIGS. 1 and 2.

(2) Image Generation

Microscopic images of nonwoven specimens are taken by an optical microscope, 3CCD optical microscopy-Keyence VHX5000 or equivalent, and are used to measure a height of a nonwoven.

The nonwoven specimen is placed on the microscope stage using double-sided conductive tape or clapped to fix the specimen. An appropriate magnification can be chosen such that features in the nonwoven specimen are suitably clear and enlarged for measurement.

(3) Height Measurement

Referring to FIG. 2, draw a line L1 contacting the apex of a protrusion 2 in the protrusion 2. Then, draw a line L2 contacting the bottom apex the protrusion 2 in parallel to line L1. A distance between line L1 and line 2 is measured and reported as a nonwoven height h. A height to the nearest 0.01 mm is reported. For each nonwoven sample, 3 images of different nonwoven cross section parts are tested. The reported value is the average of the 3 recorded measurements for each nonwoven.

2. Shape Memory Index Test (1) Fresh Height

A fresh height in a nonwoven at a fresh condition, are measured according to Nonwoven Height Test after the nonwoven is conditioned for 3 hrs under pressure of 12 KPa.

(2) Recovered Height

A recovered height in a nonwoven at recovered condition, are measured according to Nonwoven Height Test after heat-treating the fresh conditioned nonwoven samples at 90° C. for 10 secs in an oven chamber.

(3) Shape Memory Index

Shape memory index of a nonwoven is calculated according to the equitation (I).

$$\text{Shape memory index (\%)} = (\text{recovered height/fresh height}) \times 100 \qquad (I)$$

3. Concave Depth Test

Figure 16:
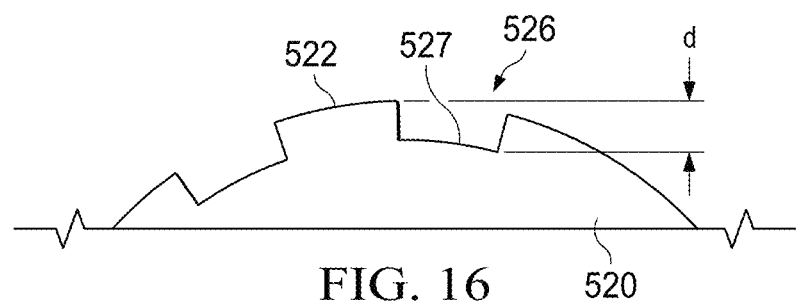
FIG. 16 is a schematic illustration of a measuring a depth of a concave on a first roll.

A depth of a concave in the roll is measured using a vernier caliper such as Mitutoyo IP66 CD-20PS or equivalent). Referring to FIG. 16, a depth d of a concave 526 of a roll 520 is a distance between a surface 522 of the roll 520 and a bottom 527 of the concave 526.

4. Concave Area Test

The area of a concave in a roll is measured using an area calculation tool of software program such as adobe acrobat reader DC, AutoCAD, Image J and equivalent to draw a closed area figure along the inner edge of the pattern.

EXAMPLES

Example 1: Nonwoven Preparation

Nonwovens 1-5 were produced using fibrous webs, and apparatus of a pair of rolls indicated in Table 1. For each of Nonwovens 1-5, a composite nonwoven web was fabricated using parallel carding machines by laying a first fibrous web on a conveyor belt and overlaying a second fibrous web on the first fibrous web. Each composite nonwoven web was heat-treated at the temperatures 130-140° C. using a hot air through-type thermal treatment apparatus using a conventional process to produce a precursor nonwoven. The precursor nonwoven was put into a mechanical aperturing process comprising a pair of rolls. Nonwoven 1 was produced using a pair of rolls of FIG. 7. Nonwovens 2 and 3 were produced using a pair of a first roll 520 and a second roll 530 shown in FIG. 10. Nonwoven 2, an exemplary nonwoven of the present invention, is a nonwoven produced by a bottom half of the first roll 520 and the second roll 530, and Nonwoven 3, a comparison nonwoven, is a nonwoven produced by a upper half of the first roll 520 and the second roll 530. Nonwovens 4 and 5 were produced using a pair of a first roll 520 and a second roll 530 shown in FIG. 11. Nonwoven 4, an exemplary nonwoven of the present invention, is a nonwoven produced by a bottom half of the first roll 520 and the second roll 530, and Nonwoven 5, a comparison nonwoven, is a nonwoven produced by a upper half of the first roll 520 and the second roll 530.

TABLE 1

|  |  | Nonwoven 1 | Nonwoven 2 | Nonwoven 3 | Nonwoven 4 | Nonwoven 5 |
|---|---|---|---|---|---|---|
| First fibrous web (25 gsm) | Fiber | PE/PET carded | PE/PET carded | PE/PET carded | PE/PET carded | PE/PET carded |
|  | Fiber fineness (denier) | 2.0 | 2.0 | 2.0 | 2.0 | 2.0 |
| Second fibrous web (15 gsm) | Fiber | PE/PP carded | PE/PP carded | PE/PP carded | PE/PP carded | PE/PP carded |
|  | Fiber fineness (denier) | 2.0 | 2.0 | 2.0 | 2.0 | 2.0 |
| Apparatus |  | FIG. 7 | FIG. 10 | FIG. 10 | FIG. 11 | FIG. 11 |
| Concave depth (mm) |  | 1 | 1 | 0 | 1 | 0 |
| Concave area (mm$^2$) |  | 155 | 187 | 0 | 97 | 0 |
| 3D Pattern |  | FIG. 1 | FIG. 3 | Same as FIG. 3 | FIG. 4 | Same as FIG. 4 |

All PE/PET fibers: ETC323, JNC corporation, China
All PE/PP fibers: TA21, Jiangnan Fiber, China Example 2. Nonwoven Properties Fresh heights and recovered heights pf the obtained Nonwovens 1-5 were measured according to Nonwoven Height Test disclosed herein. Fresh heights of nonwovens were measured after nonwovens were conditioned for 3 hrs under pressure of 12 KPa. Recovered heights of nonwovens were measured after heat-treating the fresh conditioned nonwovens at 90° C. for 10 secs in an oven chamber. Shape Memory Index (%) of each nonwoven was calculated according to the equitation (I).

$$\text{Shape memory index (\%)} = (\text{recovered height/fresh height}) \times 100 \quad (I)$$

Results are shown in Table 2 below.

TABLE 2

|  | Nonwoven 1 | Nonwoven 2 | Nonwoven 3 | Nonwoven 4 | Nonwoven 5 |
|---|---|---|---|---|---|
| Fresh height (mm) | 1709 | 1732 | 1529 | 1458 | 209 |
| Recovered height (mm) | 2138 | 2164 | 1671 | 1910 | 210 |
| Shape Memory Index (%) | 125 | 125 | 109 | 131 | 100 |

Figure 12A:
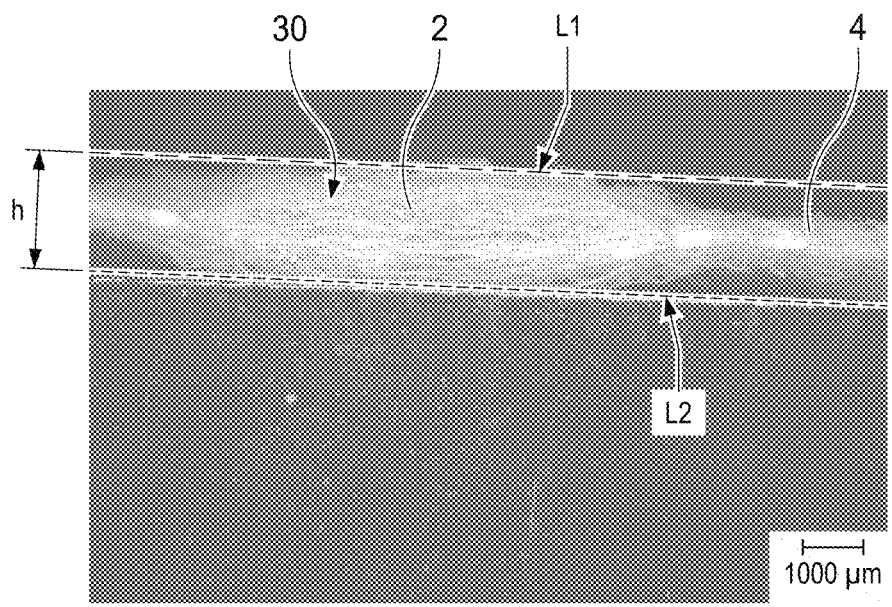
FIGS. 12A and 12B are microscopic images of cross section views of fresh Nonwoven 2 and reloft Nonwoven 2, respectively.
Figure 12B:
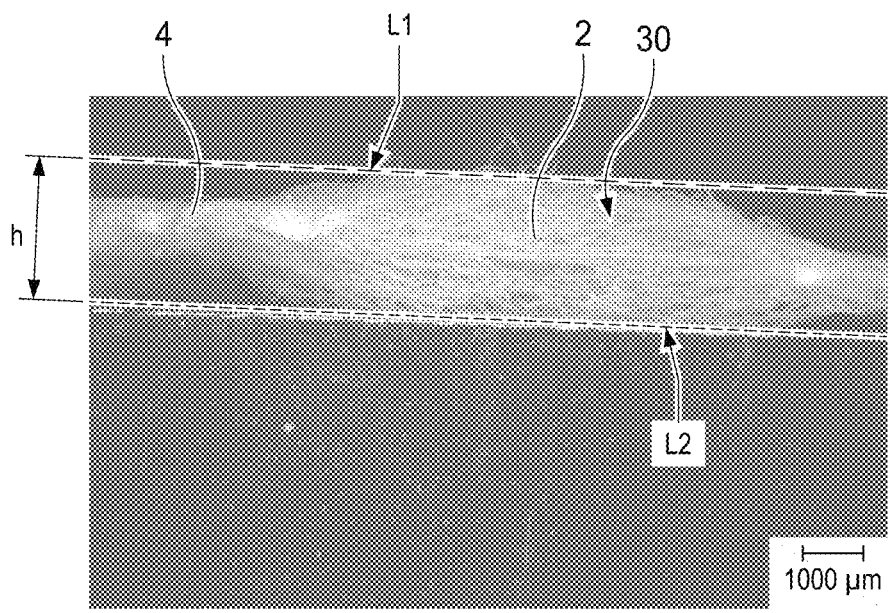
Figure 13A:
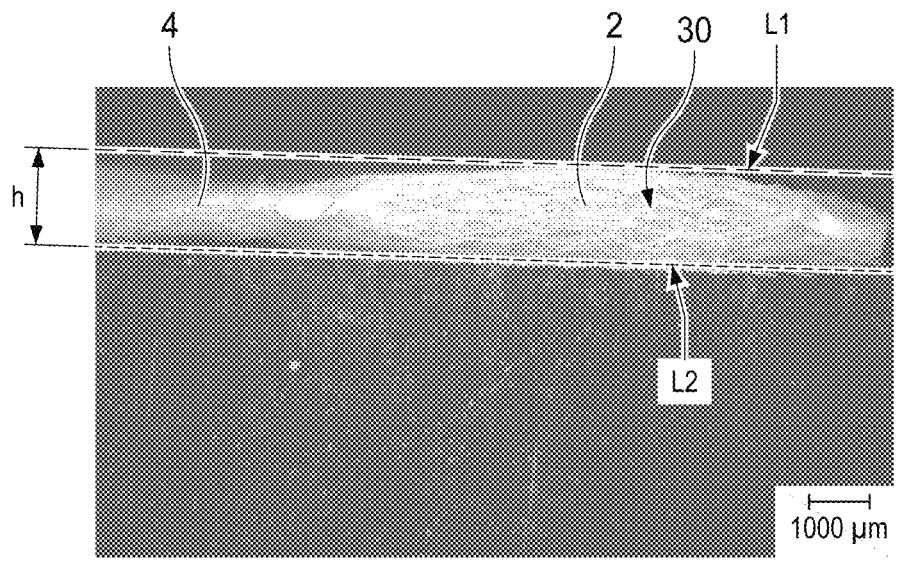
FIGS. 13A and 13B are microscopic images of cross section views of fresh Nonwoven 3 and reloft Nonwoven 3, respectively.
Figure 13B:
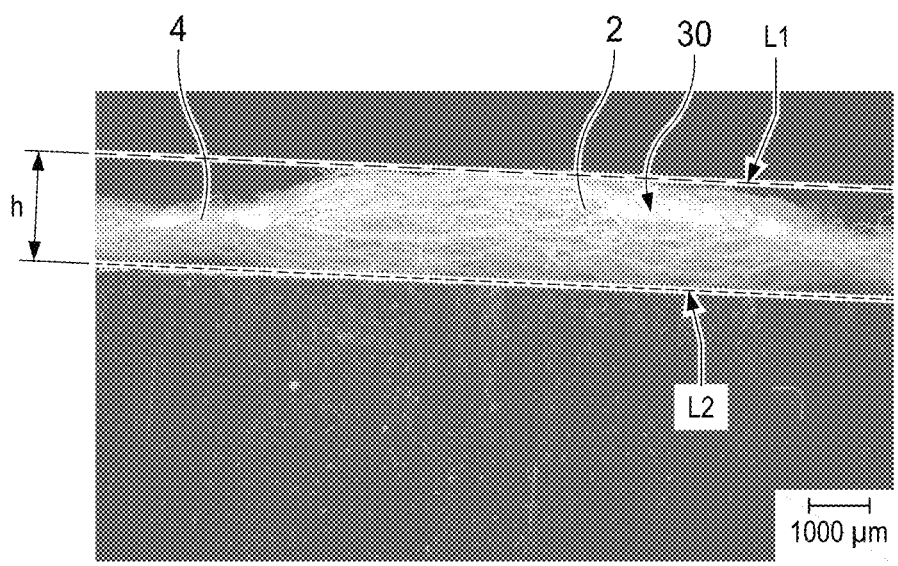

FIGS. 12A and 12B are microscopic images of cross section views of Nonwoven 2 showing nonwoven heights at fresh nonwoven and reloft nonwoven, respectively. FIGS. 13A and 13B are microscopic images of cross section views of Nonwoven 3 showing nonwoven heights at fresh nonwoven and reloft nonwoven, respectively. Nonwoven 2 has a height higher than Nonwoven 3 both in fresh nonwoven and reloft nonwoven. The height difference between Nonwoven 2 and Nonwoven 3 is more significant when the nonwovens are relofted.

Figure 14A:
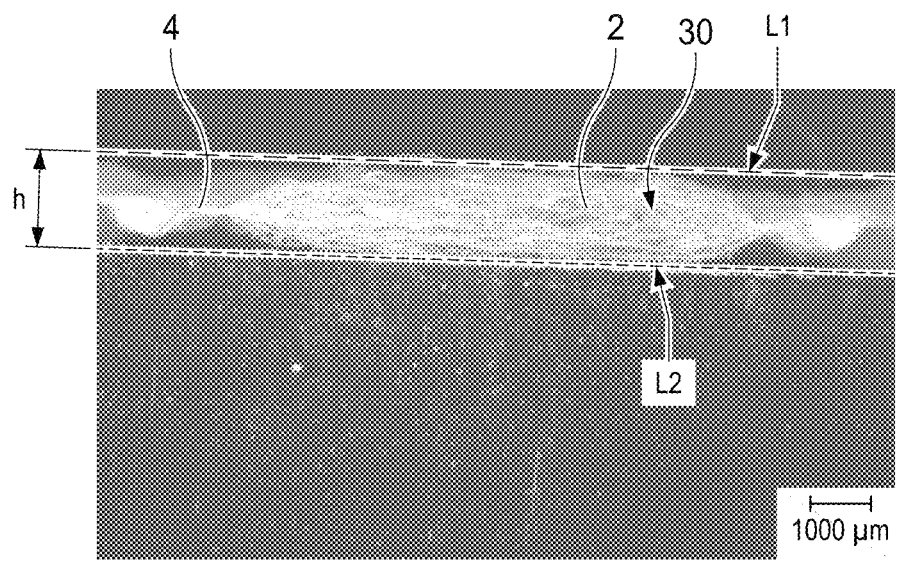
FIGS. 14A and 14B are microscopic images of cross section views of fresh Nonwoven 4 and reloft Nonwoven 4, respectively.
Figure 14B:
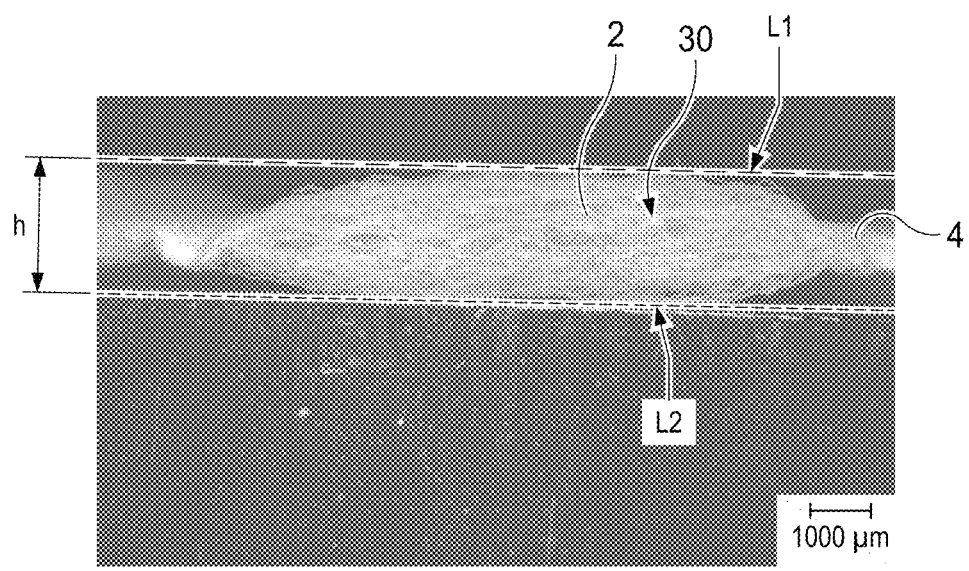
Figure 15A:
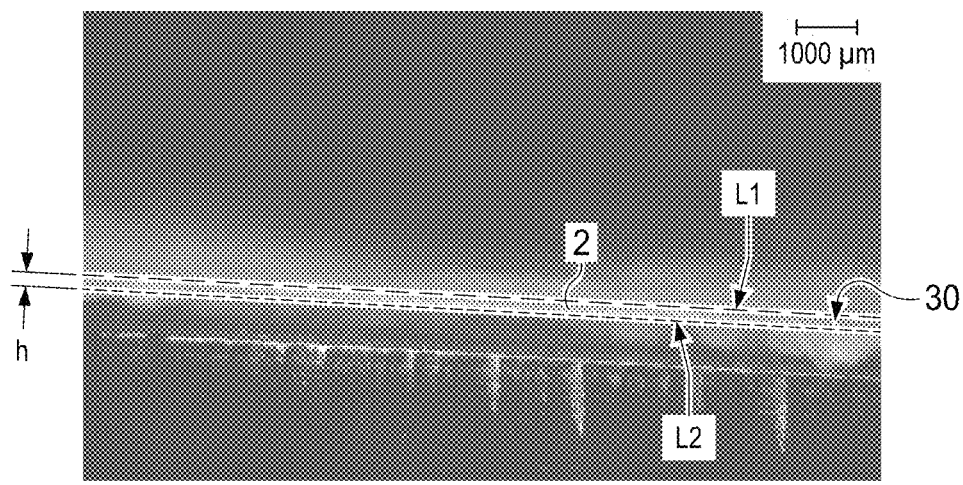
FIGS. 15A and 15B are microscopic images of cross section views of fresh Nonwoven 5 and reloft Nonwoven 5, respectively.
Figure 15B:
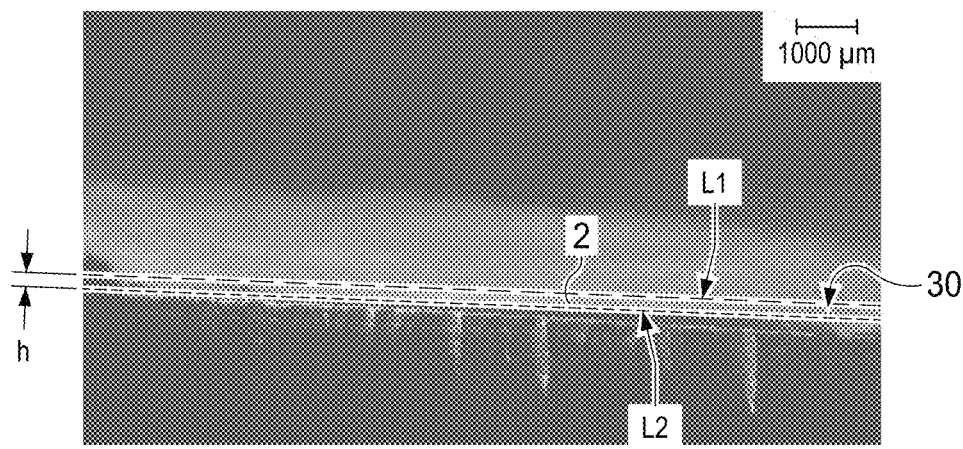

FIGS. 14A and 14B are microscopic images of cross section views of Nonwoven 4 showing nonwoven heights at fresh nonwoven and reloft nonwoven, respectively. FIGS. 15A and 15B are microscopic images of cross section views of Nonwoven 5 showing nonwoven heights at fresh nonwoven and reloft nonwoven, respectively. Nonwoven 4 has a height higher than Nonwoven 5 both in fresh nonwoven and reloft nonwoven. The height difference between Nonwoven 4 and Nonwoven 5 is more significant when the nonwovens are relofted.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus comprising a pair of counter-rotating rolls that form a nip therebetween, the pair of rolls comprising:
   a) a first roll comprising
      a surface,
      a plurality of projections extending radially outwardly from the surface of the first roll, and
      a plurality of concaves formed inwardly from the surface of the first roll;
      wherein at least one of the concaves is substantially surrounded by some of the projections; wherein the plurality of concaves each have an area no less than about 50 mm$^2$; and
   b) a second roll comprising a surface;
      wherein the plurality of concaves are configured to correspond to the surface on the second roll when the first roll and the second roll are intermeshed; and
      wherein the plurality of concaves have a recessed bottom.

2. The apparatus of claim 1, wherein the concaves have a depth no less than about 0.5 mm.

3. The apparatus of claim 1, wherein the second roll further comprises a plurality of recesses formed inwardly from the surface of the second roll, the recesses defining zones on the surface of the second roll, wherein the recesses are configured to at least partially receive the projections on the first roll when the first roll and the second roll are intermeshed.

4. The apparatus of claim 1, wherein the projections of the first roll are aperture-forming elements.

5. The apparatus of claim 1, wherein the concaves are discrete in a machine direction and a cross-machine direction.

6. The apparatus of claim 1, wherein the projections on the first roll comprises at least one projection having at least three adjacent projections, wherein the one projection and each of the at least three adjacent projections has an edge to edge space no greater than about 3 mm.

7. The apparatus of claim 1, wherein at least one of the first roll and the second roll is heated.

8. A process for producing a deformed nonwoven comprising the steps of:
   (a) forming a fibrous web;
   (b) subjecting the fibrous web to bonding treatment to bond at least part of fibers constituting the fibrous web to obtain a precursor nonwoven; and
   (c) subjecting the precursor nonwoven to a deformation forming unit comprising a pair of rolls that form a nip therebetween to form a three dimensional nonwoven, wherein the pair of rolls comprises:
      a first roll comprising
         a surface,
         a plurality of projections extending radially outwardly from the surface of the first roll, and
         a plurality of concaves formed inwardly from the surface of the first roll; wherein the plurality of concaves each have an area no less than about 50 mm$^2$; and
      a second roll comprising a surface;
      wherein the plurality of concaves of the first roll and the surface of the second roll form a protrusion on the three dimensional nonwoven;
      wherein the protrusion on the three dimensional nonwoven is substantially filled with fibers and has substantially no hollow space; and
      wherein the plurality of concaves have a recessed bottom.

9. The process of claim 8, wherein the second roll further comprises a plurality of recesses formed inwardly from the surface of the second roll, the recesses defining zones on the surface of the second roll, wherein the recesses are configured with the projections of the first roll.

10. The process of claim 8, wherein the projections of the first roll are pins so that the projections of the first roll and the recesses of the second roll form apertures on the three dimensional nonwoven.

11. The process of claim 8, wherein the fibrous web is a composite web comprising a first fibrous web and a second fibrous web.

12. The process of claim 8, wherein the process further comprises:
   (d) subjecting the deformed nonwoven to a heating unit to increase bulkiness of the deformed nonwoven.

13. The apparatus of claim 1, wherein the plurality of concaves comprises an irregular shape.

14. The apparatus of claim 1, where the at least one of the concaves is surrounded by at least five of the projections.

15. The apparatus of claim 1, wherein the second roll further comprises:
   a plurality of recesses for receiving the plurality of projections; and
   a plurality of zones, wherein the shape of at least one zone is defined by five or more of the recesses.

16. The apparatus of claim 15, wherein a portion of the surface of the first roll surrounds each recess in the second roll in a nip between the first and the second roll.

17. The apparatus of claim 1, wherein the surface surrounds each of the plurality of concaves.

18. The apparatus of claim 8, wherein the surface surrounds each of the plurality of concaves.

* * * * *